United States Patent
Montes de Oca Balderas et al.

(10) Patent No.: US 9,815,240 B2
(45) Date of Patent: Nov. 14, 2017

(54) EXPANSION MOULDING OF SHAPE MEMORY POLYMERS

(75) Inventors: Horacio Montes de Oca Balderas, York (GB); Malcolm Brown, Oiley (GB)

(73) Assignee: Smith & Nephew, Inc., Memphis, TN (US)

( * ) Notice: Subject to any disclaimer, the term of this patent is extended or adjusted under 35 U.S.C. 154(b) by 700 days.

(21) Appl. No.: 12/596,525

(22) PCT Filed: Apr. 16, 2008

(86) PCT No.: PCT/GB2008/001331
§ 371 (c)(1),
(2), (4) Date: Feb. 5, 2010

(87) PCT Pub. No.: WO2008/129245
PCT Pub. Date: Oct. 30, 2008

(65) Prior Publication Data
US 2010/0136648 A1   Jun. 3, 2010

(30) Foreign Application Priority Data

Apr. 18, 2007 (GB) .................................. 0707467.7
Dec. 12, 2007 (GB) .................................. 0724216.7

(51) Int. Cl.
B29C 61/06 (2006.01)
B29C 61/00 (2006.01)
B29C 61/04 (2006.01)
A61L 31/14 (2006.01)
C08L 67/04 (2006.01)

(52) U.S. Cl.
CPC ............ *B29C 61/06* (2013.01); *B29C 61/006* (2013.01); *B29C 61/04* (2013.01); *A61L 31/14* (2013.01); *A61L 2400/16* (2013.01); *C08L 67/04* (2013.01)

(58) Field of Classification Search
CPC ...... A61L 2400/16; A61L 31/14; A61L 31/16; C08L 67/04; A61B 2017/00867; B29C 61/06
USPC ......... 435/180; 523/105; 528/272, 310, 300, 528/354
See application file for complete search history.

(56) References Cited

U.S. PATENT DOCUMENTS

| | | |
|---|---|---|
| 3,531,561 A | 9/1970 | Trehu |
| 3,636,956 A | 1/1972 | Schneider |
| 3,736,646 A | 6/1973 | Schmitt et al. |
| 3,797,499 A | 3/1974 | Schneider |
| 3,856,905 A | 12/1974 | Dawson |
| 3,926,459 A | 12/1975 | Pontigny |
| 4,137,921 A | 2/1979 | Okuzumi et al. |
| 4,181,983 A | 1/1980 | Kulkarni |
| 4,438,253 A | 3/1984 | Casey et al. |
| 4,523,591 A | 6/1985 | Kaplan et al. |
| 4,539,981 A | 9/1985 | Tung |
| 4,559,945 A | 12/1985 | Koelmel et al. |
| 4,636,215 A | 1/1987 | Schwartz |
| 4,700,704 A | 10/1987 | Jamiolkowski et al. |
| 4,756,307 A | 7/1988 | Crowninshield |
| 4,916,207 A | 4/1990 | Boyle, Jr. et al. |
| 4,938,763 A | 7/1990 | Dunn et al. |
| 4,950,258 A | 8/1990 | Kawai et al. |
| 4,968,317 A | 11/1990 | Tormala et al. |
| 4,990,161 A | 2/1991 | Kampner |
| 5,049,591 A | 9/1991 | Hayashi et al. |
| 5,053,035 A | 10/1991 | Mclaren |
| 5,061,181 A | 10/1991 | Niznick |
| 5,108,289 A | 4/1992 | Fukuyo |
| 5,108,755 A | 4/1992 | Daniels et al. |
| 5,110,852 A | 5/1992 | Gogolewski et al. |
| 5,192,301 A | 3/1993 | Kamiya et al. |
| 5,201,771 A | 4/1993 | Belykh et al. |
| 5,208,305 A | 5/1993 | Grootaert |
| 5,250,584 A | 10/1993 | Ikada et al. |
| 5,266,608 A | 11/1993 | Katz et al. |
| 5,275,601 A | 1/1994 | Gogolewski et al. |
| 5,294,395 A | 3/1994 | Broyer |
| 5,324,308 A | 6/1994 | Pierce |
| 5,333,624 A | 8/1994 | Tovey |
| 5,360,448 A | 11/1994 | Thramann |
| 5,364,400 A | 11/1994 | Rego, Jr. et al. |
| 5,376,120 A | 12/1994 | Sarver et al. |
| 5,383,931 A | 1/1995 | Hehli et al. |
| 5,407,445 A | 4/1995 | Tautvydas et al. |

(Continued)

FOREIGN PATENT DOCUMENTS

| | | |
|---|---|---|
| AU | 2008240418 | 4/2008 |
| CA | 2254002 A1 | 5/2000 |

(Continued)

OTHER PUBLICATIONS

Song et al ("Double buble tubular film extrusion of polybutylene terephthalate-polyethylene terephthalate blends", Publication of Society of Plastic Engineers, Dec. 1999).*
International Search Report and Written Opinion for PCT/GB2008/001331 dated Aug. 25, 2008.
Australian Office Action regarding Australian Patent Application No. 2008240418 dated Dec. 2, 2011.
Andriano, et al., 'Processing and characterization of absorbable polylactide polymers for use in surgical implants,' Journal of Applied Biomaterials, 5(2):133-140 (1994).
Asano, et al., 'In vivo characteristics of low molecular weight copoly(D.L-lactic acid) formulations with controlled release of LH-RH agonist,' Biomaterials, 10(8):569-573 (1989).

(Continued)

*Primary Examiner* — Gregory Listvoyb
(74) *Attorney, Agent, or Firm* — Burns & Levinson LLP; Joseph M. Maraia

(57) ABSTRACT

The present invention relates to shape memory materials and to a method for controlling shape change in shape memory materials. In particular, the invention relates to a method and a system for forming complex shapes from shape memory materials and to shape memory materials having complex shapes.

14 Claims, 5 Drawing Sheets

(56) References Cited

U.S. PATENT DOCUMENTS

| | | |
|---|---|---|
| 5,417,712 A | 5/1995 | Whittaker et al. |
| 5,437,918 A | 8/1995 | Taniguchi et al. |
| 5,441,515 A | 8/1995 | Khosravi et al. |
| 5,458,653 A | 10/1995 | Davidson |
| 5,470,334 A | 11/1995 | Ross et al. |
| 5,525,706 A | 6/1996 | Gruber et al. |
| 5,527,337 A | 6/1996 | Stack et al. |
| 5,527,341 A | 6/1996 | Gogolewski et al. |
| 5,562,704 A | 10/1996 | Tamminmaki et al. |
| 5,567,431 A | 10/1996 | Vert et al. |
| 5,569,250 A | 10/1996 | Sarver et al. |
| 5,571,193 A | 11/1996 | Kampner |
| 5,571,204 A | 11/1996 | Nies |
| 5,633,002 A | 5/1997 | Stricker et al. |
| 5,634,936 A | 6/1997 | Linden et al. |
| 5,641,502 A | 6/1997 | Skalla et al. |
| 5,660,846 A | 8/1997 | Cheikh |
| 5,665,831 A | 9/1997 | Neuenschwander et al. |
| 5,670,161 A | 9/1997 | Healy et al. |
| 5,676,699 A | 10/1997 | Gogolewski et al. |
| 5,690,671 A | 11/1997 | McGurk et al. |
| 5,695,497 A | 12/1997 | Stahelin |
| 5,700,901 A | 12/1997 | Hurst et al. |
| 5,716,410 A | 2/1998 | Wang et al. |
| 5,716,413 A | 2/1998 | Walter et al. |
| 5,733,330 A | 3/1998 | Cox |
| 5,741,329 A | 4/1998 | Agrawal et al. |
| 5,760,118 A | 6/1998 | Sinclair et al. |
| 5,766,239 A | 6/1998 | Cox |
| 5,766,618 A | 6/1998 | Laurencin et al. |
| 5,792,400 A | 8/1998 | Talja et al. |
| 5,817,328 A | 10/1998 | Gresser et al. |
| 5,834,582 A | 11/1998 | Sinclair et al. |
| 5,837,276 A | 11/1998 | Cheikh |
| 5,853,639 A | 12/1998 | Kawakami et al. |
| 5,863,297 A | 1/1999 | Walter et al. |
| 5,868,746 A | 2/1999 | Sarver et al. |
| 5,893,850 A | 4/1999 | Cachia |
| 5,902,599 A | 5/1999 | Anseth et al. |
| 5,904,658 A | 5/1999 | Niederauer et al. |
| 5,908,918 A | 6/1999 | Chen et al. |
| 5,935,172 A | 8/1999 | Ochoa et al. |
| 5,939,453 A | 8/1999 | Heiler et al. |
| 5,947,893 A | 9/1999 | Agrawal et al. |
| 5,951,288 A | 9/1999 | Sawa |
| 5,968,092 A | 10/1999 | Buscemi et al. |
| 5,977,204 A | 11/1999 | Boyan et al. |
| 5,980,564 A | 11/1999 | Stinson |
| 5,997,580 A | 12/1999 | Mastrorio et al. |
| 5,997,582 A | 12/1999 | Weiss |
| 6,001,100 A | 12/1999 | Sherman et al. |
| 6,001,101 A | 12/1999 | Augagneur et al. |
| 6,005,161 A | 12/1999 | Brekke et al. |
| 6,071,982 A | 6/2000 | Wise et al. |
| 6,077,989 A | 6/2000 | Kandel et al. |
| 6,113,624 A | 9/2000 | Bezwada et al. |
| 6,136,369 A | 10/2000 | Leitao et al. |
| 6,150,497 A | 11/2000 | Sastry et al. |
| 6,156,842 A | 12/2000 | Hoenig et al. |
| 6,160,084 A | 12/2000 | Langer et al. |
| 6,162,225 A | 12/2000 | Gertzman et al. |
| 6,168,570 B1 | 1/2001 | Ferrera |
| 6,179,842 B1 | 1/2001 | Spotorno et al. |
| 6,203,573 B1 | 3/2001 | Walter et al. |
| 6,206,883 B1 | 3/2001 | Tunc |
| 6,248,108 B1 | 6/2001 | Tormala et al. |
| 6,248,430 B1 | 6/2001 | Toyoda et al. |
| 6,277,390 B1 | 8/2001 | Schaffner |
| 6,281,262 B1 * | 8/2001 | Shikinami ............ 523/105 |
| 6,283,973 B1 | 9/2001 | Hubbard et al. |
| 6,293,950 B1 | 9/2001 | Lynch et al. |
| 6,299,448 B1 | 10/2001 | Zdrahala et al. |
| 6,303,697 B1 | 10/2001 | Yuan et al. |
| 6,315,788 B1 | 11/2001 | Roby |
| 6,344,496 B1 | 2/2002 | Niederauer et al. |
| 6,375,465 B1 | 4/2002 | Engman et al. |
| 6,388,043 B1 | 5/2002 | Langer et al. |
| 6,406,498 B1 | 6/2002 | Tormala et al. |
| 6,425,923 B1 | 7/2002 | Stalcup et al. |
| 6,436,136 B1 | 8/2002 | Flodin et al. |
| 6,447,515 B1 | 9/2002 | Meldrum |
| 6,468,277 B1 | 10/2002 | Justin et al. |
| 6,486,296 B1 | 11/2002 | Shimamoto et al. |
| 6,488,938 B1 | 12/2002 | Ogura et al. |
| 6,503,278 B1 | 1/2003 | Pohjonen et al. |
| 6,508,830 B2 | 1/2003 | Steiner |
| 6,511,511 B1 | 1/2003 | Slivka et al. |
| 6,514,286 B1 | 2/2003 | Leatherbury et al. |
| 6,547,792 B1 | 4/2003 | Tsuji et al. |
| 6,565,606 B1 | 5/2003 | Bruce et al. |
| 6,579,533 B1 | 6/2003 | Tormala et al. |
| 6,583,232 B1 | 6/2003 | Brown |
| 6,599,323 B2 | 7/2003 | Meliean et al. |
| 6,605,090 B1 | 8/2003 | Trieu et al. |
| 6,613,089 B1 | 9/2003 | Estes et al. |
| 6,623,487 B1 | 9/2003 | Goshert |
| 6,652,582 B1 | 11/2003 | Stinson |
| 6,716,957 B2 | 4/2004 | Tunc |
| 6,719,935 B2 | 4/2004 | Tunc |
| 6,720,402 B2 | 4/2004 | Langer et al. |
| 6,726,696 B1 | 4/2004 | Houser et al. |
| 6,758,862 B2 | 7/2004 | Berry et al. |
| 6,758,863 B2 | 7/2004 | Estes et al. |
| 6,783,712 B2 | 8/2004 | Slivka et al. |
| 6,827,743 B2 | 12/2004 | Eisennann et al. |
| 6,830,575 B2 | 12/2004 | Stenzel et al. |
| 6,841,111 B2 | 1/2005 | Rickner et al. |
| 6,843,799 B2 | 1/2005 | Bartlett |
| 6,852,825 B2 | 2/2005 | Lendlein et al. |
| 6,869,445 B1 | 3/2005 | Johnson |
| 6,881,766 B2 | 4/2005 | Hain |
| 6,902,584 B2 | 6/2005 | Kwan et al. |
| 6,908,466 B1 | 6/2005 | Bonutti et al. |
| 6,908,624 B2 | 6/2005 | Hossainy et al. |
| 6,916,321 B2 | 7/2005 | TenHuisen et al. |
| 6,951,956 B2 | 10/2005 | Yamane et al. |
| 6,974,862 B2 | 12/2005 | Ringeisen et al. |
| 7,012,106 B2 | 3/2006 | Yuan et al. |
| 7,033,603 B2 | 4/2006 | Nelson et al. |
| 7,192,443 B2 | 3/2007 | Solem et al. |
| 7,208,550 B2 | 4/2007 | Mather et al. |
| 7,214,765 B2 | 5/2007 | Ringeisen et al. |
| 7,261,716 B2 | 8/2007 | Strobel et al. |
| 7,261,734 B2 | 8/2007 | Gellman et al. |
| 7,268,205 B2 | 9/2007 | Williams et al. |
| 7,270,813 B2 | 9/2007 | Shimp et al. |
| 7,285,087 B2 | 10/2007 | Moaddeb et al. |
| 7,285,130 B2 | 10/2007 | Austin |
| 7,314,480 B2 | 1/2008 | Eidenschink et al. |
| 7,335,375 B2 | 2/2008 | Li et al. |
| 7,378,144 B2 | 5/2008 | DeMeo et al. |
| 7,455,674 B2 | 11/2008 | Rose |
| 7,524,891 B2 | 4/2009 | Rose |
| 7,553,923 B2 | 6/2009 | Williams et al. |
| 8,501,215 B2 | 8/2013 | Chen et al. |
| 2001/0012940 A1 | 8/2001 | Tunc |
| 2001/0018614 A1 | 8/2001 | Bianchi |
| 2002/0022588 A1 | 2/2002 | Wilkie et al. |
| 2002/0029041 A1 | 3/2002 | Hover et al. |
| 2002/0029043 A1 | 3/2002 | Ahrens et al. |
| 2002/0071822 A1 | 6/2002 | Uhrich |
| 2002/0082362 A1 | 6/2002 | Broccini et al. |
| 2002/0120348 A1 | 8/2002 | Melican et al. |
| 2002/0138154 A1 | 9/2002 | Li et al. |
| 2002/0143403 A1 | 10/2002 | Vaidyanathan et al. |
| 2002/0150775 A1 | 10/2002 | Ishikawa et al. |
| 2002/0160032 A1 | 10/2002 | Long et al. |
| 2003/0045941 A1 | 3/2003 | Lewallen |
| 2003/0055198 A1 | 3/2003 | Langer et al. |
| 2003/0104031 A1 | 6/2003 | Dumont et al. |
| 2003/0114937 A1 | 6/2003 | Leatherbury et al. |
| 2003/0120280 A1 | 6/2003 | Roller et al. |
| 2003/0125745 A1 | 7/2003 | Tseng et al. |
| 2003/0130742 A1 | 7/2003 | Connelly et al. |

(56) References Cited

U.S. PATENT DOCUMENTS

| | | |
|---|---|---|
| 2003/0153971 A1 | 8/2003 | Chandrasekaran |
| 2003/0153972 A1 | 8/2003 | Helmus |
| 2003/0180344 A1 | 9/2003 | Wise et al. |
| 2003/0236573 A1 | 12/2003 | Evans et al. |
| 2004/0002770 A1 | 1/2004 | King et al. |
| 2004/0015187 A1 | 1/2004 | Lendlein et al. |
| 2004/0019386 A1 | 1/2004 | Ferree |
| 2004/0030341 A1 | 2/2004 | Aeschlimann et al. |
| 2004/0030342 A1 | 2/2004 | Trieu et al. |
| 2004/0052992 A1 | 3/2004 | Boone et al. |
| 2004/0054372 A1 | 3/2004 | Corden et al. |
| 2004/0106734 A1 | 6/2004 | Rose |
| 2004/0109823 A1 | 6/2004 | Kaplan |
| 2004/0110285 A1 | 6/2004 | Lendlein et al. |
| 2004/0115239 A1 | 6/2004 | Shastri et al. |
| 2004/0131681 A1 | 7/2004 | Ambrose et al. |
| 2004/0143221 A1 | 7/2004 | Shadduck |
| 2004/0153075 A1 | 8/2004 | Roger |
| 2004/0156878 A1 | 8/2004 | Rezania et al. |
| 2004/0172118 A1 | 9/2004 | Gibson |
| 2004/0193154 A1 | 9/2004 | Leatherbury et al. |
| 2004/0241203 A1 | 12/2004 | Shakesheff et al. |
| 2004/0242722 A1 | 12/2004 | Rose |
| 2004/0254639 A1 | 12/2004 | Li et al. |
| 2004/0258732 A1 | 12/2004 | Shikinami |
| 2004/0259972 A1 | 12/2004 | Ringeisen et al. |
| 2004/0260398 A1 | 12/2004 | Kelman |
| 2004/0265385 A1 | 12/2004 | West |
| 2004/0267263 A1 | 12/2004 | May |
| 2005/0008672 A1 | 1/2005 | Winterbottom et al. |
| 2005/0013793 A1 | 1/2005 | Beckman et al. |
| 2005/0019404 A1 | 1/2005 | Sung et al. |
| 2005/0033295 A1 | 2/2005 | Wisnewski |
| 2005/0043751 A1 | 2/2005 | Phan et al. |
| 2005/0043752 A1 | 2/2005 | Phan et al. |
| 2005/0070928 A1 | 3/2005 | Heino et al. |
| 2005/0080483 A1 | 4/2005 | Solem et al. |
| 2005/0080489 A1 | 4/2005 | Estes et al. |
| 2005/0085313 A1 | 4/2005 | Nishitani |
| 2005/0085812 A1 | 4/2005 | Sherman et al. |
| 2005/0090861 A1 | 4/2005 | Porter |
| 2005/0107886 A1 | 5/2005 | Crabtree et al. |
| 2005/0123582 A1* | 6/2005 | Sung et al. .......... 424/426 |
| 2005/0125051 A1 | 6/2005 | Eidenschink et al. |
| 2005/0136764 A1 | 6/2005 | Sherman et al. |
| 2005/0137611 A1 | 6/2005 | Escudero et al. |
| 2005/0137715 A1 | 6/2005 | Phan et al. |
| 2005/0159812 A1 | 7/2005 | Dinger, III et al. |
| 2005/0165128 A1 | 7/2005 | Cohn et al. |
| 2005/0177144 A1 | 8/2005 | Phan et al. |
| 2005/0177245 A1 | 8/2005 | Leatherbury et al. |
| 2005/0182411 A1 | 8/2005 | DeMeo et al. |
| 2005/0182428 A1 | 8/2005 | Bearinger et al. |
| 2005/0187602 A1 | 8/2005 | Eidenschink |
| 2005/0196420 A1* | 9/2005 | Zucherman et al. ......... 424/423 |
| 2005/0197422 A1 | 9/2005 | Mayadunne et al. |
| 2005/0208094 A1 | 9/2005 | Armitage et al. |
| 2005/0209705 A1 | 9/2005 | Niederauer et al. |
| 2005/0240281 A1 | 10/2005 | Slivka et al. |
| 2005/0273106 A1 | 12/2005 | Oepen |
| 2006/0027612 A1 | 2/2006 | Boaron |
| 2006/0051394 A1 | 3/2006 | Moore et al. |
| 2006/0067973 A1 | 3/2006 | Schachter |
| 2006/0095138 A1 | 5/2006 | Truckai et al. |
| 2006/0121084 A1 | 6/2006 | Borden et al. |
| 2006/0121087 A1 | 6/2006 | Williams et al. |
| 2006/0136071 A1 | 6/2006 | Maspero et al. |
| 2006/0149248 A1 | 7/2006 | Schlienger et al. |
| 2006/0177480 A1 | 8/2006 | Sung et al. |
| 2006/0178739 A1* | 8/2006 | Shalaby et al. ............ 623/1.49 |
| 2006/0178748 A1 | 8/2006 | Dinger, III et al. |
| 2006/0188546 A1 | 8/2006 | Giroux |
| 2006/0188547 A1 | 8/2006 | Bezwada |
| 2006/0200150 A1 | 9/2006 | Iiomaki et al. |
| 2006/0207612 A1* | 9/2006 | Jackson et al. ............ 128/860 |
| 2006/0247610 A1 | 11/2006 | Lanphere et al. |
| 2006/0263335 A1 | 11/2006 | France et al. |
| 2006/0264948 A1 | 11/2006 | Williams |
| 2006/0293749 A1 | 12/2006 | Hudgins et al. |
| 2007/0005094 A1 | 1/2007 | Eaton et al. |
| 2007/0014831 A1 | 1/2007 | Sung et al. |
| 2007/0041950 A1 | 2/2007 | Leatherbury et al. |
| 2007/0043376 A1 | 2/2007 | Leatherbury et al. |
| 2007/0043433 A1 | 2/2007 | Chandrasekaran |
| 2007/0048383 A1 | 3/2007 | Helmus |
| 2007/0050018 A1 | 3/2007 | Wainwright |
| 2007/0065652 A1 | 3/2007 | Liebschner |
| 2007/0067043 A1 | 3/2007 | Dericks |
| 2007/0083205 A1 | 4/2007 | Attawia et al. |
| 2007/0100449 A1 | 5/2007 | O'Neil et al. |
| 2007/0128154 A1 | 6/2007 | Hadba et al. |
| 2007/0134305 A1 | 6/2007 | Zilberman |
| 2007/0141111 A1 | 6/2007 | Suokas et al. |
| 2007/0156251 A1 | 7/2007 | Karmon |
| 2007/0162019 A1 | 7/2007 | Burns et al. |
| 2007/0182041 A1 | 8/2007 | Rizk et al. |
| 2007/0191963 A1 | 8/2007 | Winterbottom et al. |
| 2007/0213828 A1 | 9/2007 | Trieu et al. |
| 2007/0260324 A1 | 11/2007 | Joshi et al. |
| 2007/0265622 A1 | 11/2007 | Aeschlimann et al. |
| 2007/0270852 A1 | 11/2007 | Tormala et al. |
| 2007/0276366 A1 | 11/2007 | Gaines, Jr. |
| 2007/0280983 A1 | 12/2007 | Strickler et al. |
| 2007/0299151 A1 | 12/2007 | Guelcher et al. |
| 2007/0299156 A1 | 12/2007 | Brown |
| 2007/0299449 A1 | 12/2007 | Allinniemi et al. |
| 2008/0015578 A1 | 1/2008 | Erickson et al. |
| 2008/0077140 A1 | 3/2008 | Osman |
| 2008/0085297 A1 | 4/2008 | Dave et al. |
| 2008/0086199 A1 | 4/2008 | Dave et al. |
| 2008/0109037 A1 | 5/2008 | Steiner et al. |
| 2008/0154368 A1 | 6/2008 | Justis et al. |
| 2008/0154373 A1 | 6/2008 | Protopsaltis et al. |
| 2008/0200638 A1 | 8/2008 | Redepenning |
| 2008/0206297 A1 | 8/2008 | Roeder et al. |
| 2008/0228186 A1 | 9/2008 | Gall et al. |
| 2008/0234754 A1 | 9/2008 | McCarthy et al. |
| 2008/0234762 A1 | 9/2008 | Forstein et al. |
| 2008/0241211 A1 | 10/2008 | Han et al. |
| 2008/0249633 A1 | 10/2008 | Wu |
| 2008/0262613 A1 | 10/2008 | Gogolewski |
| 2008/0305144 A1 | 12/2008 | Brown et al. |
| 2009/0030160 A1 | 1/2009 | Kanazawa et al. |
| 2009/0048145 A1 | 2/2009 | Hellerbrand et al. |
| 2009/0093888 A1 | 4/2009 | Dawson et al. |
| 2009/0099600 A1 | 4/2009 | Moore et al. |
| 2009/0149856 A1 | 6/2009 | Paakinaho et al. |
| 2009/0171064 A1 | 7/2009 | Arimura et al. |
| 2009/0204116 A1 | 8/2009 | Shalaby et al. |
| 2009/0270923 A1 | 10/2009 | Tormala et al. |
| 2009/0274742 A1 | 11/2009 | Brown et al. |

FOREIGN PATENT DOCUMENTS

| | | |
|---|---|---|
| CN | 1857742 A | 11/2006 |
| DE | 1604403 B1 | 11/1970 |
| DE | 2817778 A1 | 11/1978 |
| DE | 2947985 A1 | 9/1981 |
| DE | 3036611 A1 | 6/1982 |
| DE | 3936188 A1 | 5/1990 |
| DE | 4226465 A1 | 2/1993 |
| DE | 4220216 C1 | 1/1994 |
| DE | 102005032005 A1 | 1/2007 |
| EP | 204931 A1 | 12/1986 |
| EP | 299004 A1 | 1/1989 |
| EP | 0326426 A | 1/1989 |
| EP | 321389 A1 | 6/1989 |
| EP | 326426 A2 | 8/1989 |
| EP | 0404004 A | 6/1990 |
| EP | 401844 A2 | 12/1990 |
| EP | 439892 A2 | 8/1991 |
| EP | 475077 A2 | 3/1992 |
| EP | 531487 A1 | 3/1993 |
| EP | 590656 A1 | 4/1994 |

(56) References Cited

FOREIGN PATENT DOCUMENTS

| | | |
|---|---|---|
| EP | 595956 A1 | 5/1994 |
| EP | 635274 A2 | 1/1995 |
| EP | 711534 A1 | 5/1996 |
| EP | 747072 A2 | 12/1996 |
| EP | 751165 A2 | 1/1997 |
| EP | 803521 A1 | 10/1997 |
| EP | 805175 A1 | 11/1997 |
| EP | 806283 A2 | 11/1997 |
| EP | 815809 A2 | 1/1998 |
| EP | 1000958 A1 | 5/2000 |
| EP | 1009448 A2 | 6/2000 |
| EP | 1056487 A1 | 12/2000 |
| EP | 1086711 A1 | 3/2001 |
| EP | 1093774 A1 | 4/2001 |
| EP | 1136510 A1 | 9/2001 |
| EP | 1142597 A1 | 10/2001 |
| EP | 1216717 A1 | 6/2002 |
| EP | 1277482 A2 | 1/2003 |
| EP | 1284756 A1 | 2/2003 |
| FR | 2691901 A1 | 12/1993 |
| FR | 2691991 A1 | 12/1993 |
| FR | 2863478 A1 | 6/2005 |
| GB | 807589 A | 1/1959 |
| GB | 1416575 A | 12/1975 |
| GB | 2215209 A | 9/1989 |
| JP | 62-199429 | 9/1987 |
| JP | 01-192367 | 8/1989 |
| JP | H02169612 A | 6/1990 |
| JP | 02-270519 | 11/1990 |
| JP | 03-021613 | 1/1991 |
| JP | 05-147105 | 6/1993 |
| JP | 06-065460 | 3/1994 |
| JP | 06-234157 | 8/1994 |
| JP | H8196617 A | 8/1996 |
| JP | H0940761 A | 2/1997 |
| JP | H09095606 A | 4/1997 |
| JP | H09221539 A | 8/1997 |
| JP | H09234241 A | 9/1997 |
| JP | H09272790 A | 10/1997 |
| JP | H10176039 A | 6/1998 |
| JP | 10-309313 | 11/1998 |
| JP | 10309313 | 11/1998 |
| JP | H10309313 A | 11/1998 |
| JP | H11209595 A | 8/1999 |
| JP | 2003-094516 | 4/2003 |
| JP | 2003-518230 | 6/2003 |
| JP | 2006-503172 | 1/2006 |
| JP | 2007-46050 A | 2/2007 |
| KR | 0180858 B1 | 4/1999 |
| WO | 19840004311 | 11/1984 |
| WO | 1990003768 | 4/1990 |
| WO | 1993001773 | 2/1993 |
| WO | 1995034331 | 12/1995 |
| WO | 96/22061 A1 | 7/1996 |
| WO | 1997005193 | 2/1997 |
| WO | 9725936 | 7/1997 |
| WO | 97/29673 A1 | 8/1997 |
| WO | 9736555 | 10/1997 |
| WO | 98/00141 A1 | 1/1998 |
| WO | 1998026814 | 6/1998 |
| WO | 9830141 | 7/1998 |
| WO | 9847445 | 10/1998 |
| WO | 9911296 | 3/1999 |
| WO | 1999011297 | 3/1999 |
| WO | 1999022770 | 5/1999 |
| WO | 200001426 | 1/2000 |
| WO | 00/56376 A1 | 9/2000 |
| WO | 200146501 | 6/2001 |
| WO | 2001096105 | 12/2001 |
| WO | 2002000137 | 1/2002 |
| WO | 200234159 | 5/2002 |
| WO | 200234310 | 5/2002 |
| WO | 2002076725 | 10/2002 |
| WO | 3004071 | 1/2003 |
| WO | 2003057844 A2 | 7/2003 |
| WO | 2003064531 | 8/2003 |
| WO | 2004011054 | 2/2004 |
| WO | 2004071356 | 8/2004 |
| WO | 2004110313 | 12/2004 |
| WO | 2005014718 | 2/2005 |
| WO | 2005028534 | 3/2005 |
| WO | 2005046470 | 5/2005 |
| WO | 2005085313 | 9/2005 |
| WO | 2005112804 | 12/2005 |
| WO | 2006053936 | 5/2006 |
| WO | 2006064025 | 6/2006 |
| WO | 2006095138 A1 | 9/2006 |
| WO | 2006108114 | 10/2006 |
| WO | 2006114483 | 11/2006 |
| WO | 2006116129 | 1/2007 |
| WO | 2007020430 A2 | 2/2007 |
| WO | 2007020432 | 2/2007 |
| WO | 2007021593 | 2/2007 |
| WO | 2007023296 | 3/2007 |
| WO | 2007024492 | 3/2007 |
| WO | WO2007038009 A2 | 4/2007 |
| WO | 2007065074 | 6/2007 |
| WO | 2007084609 | 7/2007 |
| WO | 2007086832 | 8/2007 |
| WO | 2007111808 | 10/2007 |
| WO | 2007117499 | 10/2007 |
| WO | 2008001633 | 1/2008 |
| WO | 2008116591 | 3/2008 |
| WO | 2008044011 | 4/2008 |
| WO | 2008067531 | 6/2008 |
| WO | 2008089172 | 7/2008 |
| WO | 2008098019 | 8/2008 |
| WO | 2008101932 | 8/2008 |
| WO | 2008112875 A2 | 9/2008 |
| WO | 2008112880 A2 | 9/2008 |
| WO | 2008112912 | 9/2008 |
| WO | 2008131197 | 10/2008 |
| WO | 2008134264 | 11/2008 |

OTHER PUBLICATIONS

Barca, et al., 'Resorbable poly-L-lactic acid mini-staples for the fixation of Akin osteotomies,' The Journal of Foot and Ankle Surgery, 36(2):106-111 (1997).

Bartenev et al.; On the theory of biaxial orientation of amorphous polymers, Mechanics of Composite Materials, 1973, vol. 6, p. 671-677.

Bertrand, et al., Biocompatibility Aspects of New Stent Technology, JACC, 32(3):562-571 (1998).

Celikkaya, et al., 'Poly(DL-lactide)/Poly(ethylene glycol) Copolymer Particles. I. Preparation and Characterization,' Journal of Applied Polymer Science, 61: 1439-1446 (1996).

D. Hull and T. W. Clyne, 'An introduction to composite materials,' Second Edition, Cambridge University Press, Table of Contents, (1996) 8 pages.

D. Wheeler, et al., 'Effect of bioactive glass particle size on osseous regeneration of cancellous defects,' J. Biomed. Materials Research, 41(4):527-533 (1998).

Daniels, et al., 'Mechanical properties of biodegradable polymers and composites proposed for internal fixation of bone,' J. Applied Biomaterials, 1 :57-78 (1990).

Dauner, et al. 'Resorbable continuous-fiber reinforced polymers for osteosynthesis,' J. Materials Science Materials in Medicine, 9: 173-179 (1998).

Eling, et al., 'Biodegradable Materials of Poly(L-Lactic Acid): 1. Melt-Spun and Solution-Spun Fibres,' Polymer, 23:1587-1593 (1982).

Fambri, et al., 'Biodegradable fibres of poly(l-lactic acid) produced by melt spinning,' Polymer, 38:79-85 (1997).

Frenger, 'Biomedical Uses of Shape Memory Polymers,' Biomed. Sci. Instrum., 29:47-50 (1993).

Fukuzaki, et al., Synthesis of copoly(D,L-Lactic acid) with relatively low molecular weight and in vitro degradation, Japan Atomic Energy Research Institute, Gunma, Jpn, European Polymer Journal,25(10):1019-1026 (1989).

(56) References Cited

OTHER PUBLICATIONS

Gautier, et al., 'Poly(a-hydroxyacids) for application in the spinal cord: Resorbability and biocompatibility with adult rate Schwann cells and spinal cord,' Journal of Biomedical Materials Research, 42(4):642-654 (1998).
Giardino, et al., 'Experimental evaluation of a resorbable intramedullary plug for cemented total hip replacement,' Biomaterials, 18(13):907-913 (1997).
Gogolewsji, et al., 'Resorbable materials of poly(L-lactide). II Fibers spun from solutions of poly(L-lactide) in good solvents,' J. Appl. Polymer Sci., 28:1045-1061 (1983).
Grijpma et al., 'Chain Entanglement Mechanical Properties and Drawability of Poly (Lactide),' Colloid Polym Sci., 272: 1068-1081 (1994).
Haers, et al., 'Biodegradable polyactide plates and screws in orthognathic surgery,' Technical Note, Journal of Cranio-Maxillofacial Surgery, 26(2):87-91 (1998).
Hyon, et al., 'Effects of residual monomer on the degradation of DL-lactide polymer,' Hyon, Jamshidi & Ikada, Polymer International, 46:196-202 (1998).
J. West et al, 'Bioactive Polymers, Synthetic biodegradable polymer scaffolds,' Chapter 5, pp. 83-95, Anthony Atala and David J. Mooney, Editors; Joseph P. Vacanti and Robert Langer, Associate Editors, Birkhauser (1997).
Kaitian, et al., 'Poly(D,L-Lactic Acid) Homopolymers: Synthesis and Characterization,' Turkish Journal of Chemistry, 20:43-53 (1996).
Kister, et al., 'Effects of morphology, conformation and configuration on the IR and Raman spectra of various poly(lactic acid)s,' Polymer, 39(2): 267-273 (1998).
Koelling, et al., 'In vitro real-time aging and characterization of poly(L/D-lactic acid),' Proceedings of the 1997 1fth Southern Biomedical Engineering Conference (Cat. No. 97TH8270), pp. 197-201.
Kontio, et al., 'Fibrous wound repair associated with biodegradable poly-L/D-lactide copolymers implants: study of the expression of tenascin and cellular fibronectin,' Journal of Materials Science—Materials in Medicine, 9:10:603-609 (1988).
Kricheldorf, et al., 'Polyactones: 32. High-molecular weight polylactides by ring-opening polymerization with dibutylmagnesium or butylmagnesium chloride,' Polymer, 36(15):2995-3003 (1995).
L. L. Hench, 'Bioactive materials: The potential for tissue regeneration,' J. Biomed. Materials Research, 41(4):511-518 (1998).
Losken, et al., 'Memory of DL-polylactic acid biodegradable plates,' Ann. Plast. Surg., 32(6):606-611 (1994).
MacDonald, et al., 'Enzymatic degradability of poly(lactide): Effects of chain stereochemistry and material crystallinity,' Macromolecules, 29(23):7356-7361 (1996).
Mainil-Varlet, et al., 'Effect of in vivo and in vitro degradation on molecular and mechanical properties of various low-molecular weight polylactides,' Journal of Biomedical Materials Research, 36(3):360-380 (1997).
Matsumura, et al., 'Novel ring opening polymerization of lactide by lipase,' Macromol. Symp., 130:285-304 (1998).
Mauduit, J. et al.; "Hydrolytic degradation of films prepared from blends of high and low molecular weight poly (DL lactic acid)s" Journal of Biomedical Materials Research, 1996, vol. 30, p. 201-207.
Morita, et al., 'Intravitreous delivery of dexamethasone sodium m-sulfobenzoate from poly(DL-lactic acid) implants,' Biological & Pharmaceutical Bulletin, 21 (2): 188-190 (1998).
Okihara, et al., Crystal structure of stereocomplex of poly(L-lactide) and poly(D-lactide), Journal of Macromolecular Science—Physics, B30(1 and 2): 119-140 (1991).
Okuzaki, et al., Mechanical Properties and Structure of the Zone-Drawn Poly(l-lactic acid) Fibers, Journal of Polymer Science, Part B, Polymer Physics, 37:991-996 (1999).

Oriented Polymer Materials, Edited by Stoyko Fakirov, published by Huthig & Wepf Verlag Zug, Heidelberg, Oxford CTIUSA, Table of Contents pp. v, viii, ix-xix (1996).
Penning, et al., 'Preparation and properties of absorbable fibres from l-lactide copolymers,' Polymer, 34(5):942-951 (1993).
Pitt, et al., 'Modification of the rates of chain cleavage of polY(e-caprolactone) and related polyesters in the solid state,' Journal of Controlled Release, 4:283-292 (1987).
Pitto, et al., "Comparison of fixation of the femoral component without cement and fixation with use of a bone-vacuum cementing technique for the prevention of fat embolism during total hip arthroplasty," J. Bone Joint Surg., 81-A(6)~831-843 (1999).
Rak, et al., 'The preparation and characterization of poly(D,L-lactic acid) for use as a biodegradable drug carrier,' (1985) liverpool Poly tech., liverpool, UK, Pharmaceutica Acta Helvetiae, 60:(5-6):162-169.
Ristic, et al., 'An investigation of synthesis and degradation of poly(D,L-lactide) and controlled release of albumin from biodegradable poly(D,L-lactide) cylinders,' ICheaP-2, the second Italian conference on chemical and process engineering, Florence, pp. 559-563 (1995).
Schliephake, et al., 'Reconstruction of the mandible by prefabricated autogenous bone grafts,' Int. J. Oral Maxillofac. Surg., 26:244-252 (1997).
Stahelin, et al., Clinical degradation and biocompatibility of different bioabsorbable interference screws: a report of six cases: Arthroscopy: The Journal of Arthroscopic & Related Surgery, 13(2):238-244 (1997).
Steendam, et al., The role of elastic relaxation in drug delivery from poly(DL-lactic acid) based tablets. A shape memory phenomenon: Proceedings of the International Symposium on Controlled Release of Bioactive Materials, 25:128-129 (1998).
Stevels, et al., 'Blends van blok copolymeren die een poly(L-lactide) of poly(D-lactide) blok bevatten,' Biomedical Science and Engineering Meeting, pp. 107-110 (1994).
Structure and Properties of Oriented Polymers, Ed. I. M. Ward, Department of Physics, UniverSity of Leads, England, a Halsted Press Book, John Wiley & Sons, New York-Toronto (1975) Table of Contents.
Tagl, "Thesis—The morselized and impacted bone graft animal experiments on proteins, impaction and load," Acta Orthop. Scand. Suppl., 290:1-40 (2000).
Temenoff et al., "Injectable biodegradable materials for orthopedic tissue engineering," Biomaterials, 21 :2405-2412 (2000).
Tschakaloff, et al., 'Degradation kinetics of biodegradable DL-polyactic acid biodegradable implants depending on the site of implantation,' International Journal of Oral and Maxillofacial Surgery, 23(6 Pt2 ):443-445 (1994).
Tsuji, et al., Stereocomplex formation between enantiomeric poly(lactic acid). VIII. Complex fibers spun from mixed solution of poly(D-lactic acid) and poly(L-lactic acid), Journal of Applied Polymer Science, 51(2):337-344 (1994).
Zegzula, et al., 'Bone Formation with Use of rhBMP-2 (Recombinant Human Bone Morphogenetic Protein-2,' The Journal of Bone and Joint Surgery, 79:1778-1790 (1997).
Zhang, Biodegradable lactide polymers: synthesis, degradation, and controlled drug release properties (drug release), Queen's University at Kingston, Canada, vol. 55/01-B of Dissertation Abstracts International, p. i-xv, 1-179 (Oct. 1993).
Australian Examiner's First Report on patent application AU 2008240418 dated Dec. 2, 2011.
PCT/GB2008/001331 International Preliminary Report on Patentability with Written Opinion dated Oct. 20, 2009, 8 pages.
Summary of the Office Action, dated Mar. 19, 2012, 1 page.
Japanese 1st Office Action for Application No. 2010-503579, dated Mar. 6, 2012, 6 pages.
Japanese 2nd Office Action for Application No. 2010-503579, dated Feb. 19, 2013, 3 pages.
Office Action from related European Application No. 08736993.0-1706 dated Mar. 10, 2017.
Vert, M. et al. "Bioresorbability and biocompatibility of aliphatic polyesters", Journal of Materials Science: Materials in Medicine 3, 1992, pp. 432-446.

(56) References Cited

OTHER PUBLICATIONS

Siparsky, G.L. et al. "Water Transport in Polylactic Acid (PLA)." Journal of Environmental Polymer Degradation, vol. 5, No. 3, 1997.
Nativ, O. et al. "Bladder neck suspension using bone anchors for the treatment of female stress incontinence." ASAIO J. May-Jun. 1997;43(3):204-8.
Momma, M. et al. "Long Bone Intramedullary Fixation Method Using Shape Memory Anchoring Nails—An Attempt at a Biomechanical Test and the Application Thereof to Proximal Humeral Fractures." J. Eastern Japan Assoc. Orthopaedics & Traumatology, vol. 12, No. 4: 385-90.
Atkins, G.J. et al. "Role of polyethylene particles in peri-prosthetic osteolysis: A Review." World of Journals of Orthopedics, 2(10), Oct. 18, 2011, pp. 93-101.
Hill, R.G., "Chapter 10: Biomedical Polymers." Biomaterials, artificial organs and tissue engineering. Imperial College London, UK (2005), 7 pages. [copy unavailable].

\* cited by examiner

EXPANSION MOULDING OF SHAPE MEMORY POLYMERS

CROSS-REFERENCE TO RELATED APPLICATIONS

This application is a U.S. National Stage Application, submitted under 35 U.S.C. 371, claiming priority to PCT International Patent Application PCT/GB2008/001331 filed on Apr. 16, 2008, which claims priority to Great Britain Patent Application No. 0707467.7 filed on Apr. 18, 2007 and Great Britain Patent Application No. 0724216.7 filed on Dec. 12, 2007, the disclosures of which are incorporated herein by reference in their entirety.

FIELD OF THE INVENTION

The present invention relates to shape memory materials and to a method for controlling shape change in shape memory materials. In particular, the invention relates to a method and a system for forming complex shapes from shape memory materials and to shape memory materials having complex shapes.

RELATED ART

Shape memory polymers (SMPs) are materials that have the ability to "memorize" a "permanent" macroscopic shape, be orientated or manipulated under temperature and/or stress to a temporary or dormant shape, and then be subsequently relaxed to the original or memorized, stress-free condition or shape. Relaxation is usually prompted or encouraged by the application of thermal, electrical, or environmental energy to the manipulated or orientated SMP. This relaxation is associated with elastic deformation energy stored in the SMP during orientation of the SMP. The degree of orientation of the SMP is the driving force that causes relaxation. Thus the greater the degree of orientation, the greater will be the force or energy stored in the SMP and hence the greater will be the force or energy driving relaxation of the SMP when triggered or prompted by an external energy source.

SMPs like other polymers can be grouped into two main categories; they can be amorphous, thus lacking any regular positional order on the molecular scale, or they can be semicrystalline which contain both molecularly ordered crystalline regions and amorphous regions in the same sample.

Plastic deformation of amorphous SMPs and SMP composites results in the formation of an orientated amorphous or semi-crystalline polymer network. Orientation of SMPs and SMP composites can be achieved by stretching, drawing or applying a compressive and/or shear force to the SMP. The SMP may be orientated by application of any one or a combination of these forces and can be carried out at ambient temperatures or elevated temperatures. Generally, the temperature of the SMP is raised above ambient temperature to around the glass transition temperature (Tg) of the SMP before application of the orientation force or forces. Raising the temperature of the SMP in this way helps prevent the SMP from rupturing when the orientation force is being applied thereto. The glass transition temperature is the temperature below which the physical properties of amorphous SMPs behave in a manner similar to a solid, and above which they behave more like a rubber or liquid allowing the SMP to undergo plastic deformation without risk of fracture. After the SMP has been orientated, the temperature is reduced and the SMP is fixed in a temporary or dormant configuration.

The orientated network is physically stable well below the glass transition temperature (Tg) where molecular mobility is low. However, near or above the polymer's glass transition temperature, molecular motion rapidly increases and causes the orientated network to relax, usually accompanied by physical changes in the dimensions of the SMP. During relaxation, the orientated SMP tends to recover the original dimensions of the unorientated SMP, hence the name shape "memory" material. However, recovery of the original shape depends primarily on the degree of crystallinity, orientation, the micro and nano-structures and the conditions under which the orientated network is relaxed. For copolymers other important factors are their detailed composition and their specific thermal properties, i.e. the glass transition and melting temperatures, of their components.

It is believed that the relaxation process occurs nearly at constant volume. The degree of recovery during relaxation, for a semi-crystalline orientated SMP, depends on its crystallinity and structure and complete recovery of its original shape is difficult. In contrast, amorphous orientated SMPs, copolymers and their composites can return substantially to their original shape under appropriate relaxation conditions.

The degree of orientation is the driving force that causes relaxation. The greater the degree of orientation, i.e. the force or forces applied to the SMP, the greater will be the driving force.

During relaxation, the orientated SMP releases stored internal forces or energy. For example, an SMP of cylindrical shape orientated by applying a stretching force uniaxially along its longitudinal axis will shrink in length and expand in diameter during relaxation under free boundary conditions, i.e. where no physical constraints are imposed. Hence, when the cylindrical shaped SMP relaxes, it will induce a shrinkage force along its longitudinal axis and also an expanding force in the radial direction. These longitudinal and radial forces are proportional to the degree of orientation and mass of orientated polymer. The greater the degree of orientation, i.e. the greater the forces applied to the SMP during orientation, and the greater the mass of the SMP, the greater these longitudinal and radial relaxation forces will be. For SMPs of other geometries, the relaxation forces will also depend on the degree or magnitude of the orientation force, the direction of the applied orientation force, as well as the mass of the orientated SMP. The rate of relaxation or the rate of shape recovery of the SMP is dependent on sample geometry, processing conditions and more importantly on the mass and thermal diffusivity of the SMP.

The mechanism of the prior art whereby the shape of an SMP is altered involves applying an orientation force to the SMP. Following orientation of the SMP where the SMP is changed from a first pre-orientated shape to a second orientated shape, the orientated SMP is heated above its glass transition temperature wherein the SMP relaxes back to its original or pre-orientated shape. It is an aim of the present invention to provide a shape memory polymer with tailored relaxation characteristics, capable of relaxing back to a shape which is different to its original shape. It is a further aim of the invention to provide shape memory material with complex geometries and structural assemblies of shape memory polymers with other solid elements such as metals, polymers and ceramics.

SUMMARY OF THE INVENTION

According to a first aspect of the present invention there is provided a shape memory polymer having a first configuration and a second orientated configuration, the second orientated configuration when at least partially relaxed in a mould by stimulating molecular motion of the SMP, relaxes to a third configuration that is different to the first and second configurations.

According to a second aspect of the present invention there is further provided a method for manufacturing a pre-relaxed shape memory polymer comprising the steps of:—processing a shape memory polymer having a first configuration to form an orientated shape memory polymer having a second configuration which is different to the first configuration; at least partially relaxing the orientated shape memory polymer by stimulating molecular motion of the shape memory polymer; and controlling the conditions under which the orientated shape memory material is at least partially relaxed to form a pre-relaxed shape memory polymer having a third configuration which is different to the first and second configurations.

Generally, the term configuration refers to the shape of the SMP but may also refer solely to the dimensions of the SMP. For example, in an embodiment of the invention, the third or final shape of the SMP can be intermediate in dimension between the first shape and second orientated shape. Intermediate in dimension may refer to one or more dimensions of the shape. For example, the SMP may have an initial or first cylindrical shape having radius r and height h and may be orientated, by stretching along its longitudinal axis, to create a cylinder having a second shape with a smaller radius $r^{--}$ and larger height $h^{++}$. An example of an intermediate third shape would thus include a cylinder having a radius R and height H, where $r^{--}<R<r$ and $h<H<h^{++}$.

Preferably, the third shape is substantially different to the first and second shapes. For example, in an embodiment of the invention, the initial shape of the SMP is cylindrical and the final shape is that of a threaded screw. In another embodiment the initial shape is cylindrical and the final shape is a rod with regular polygonal cross sectional area such as, for example, a triangle, quadrilateral, or pentagon.

Preferably, the step of processing the shape memory material includes applying a stretching, or drawing or compressive force to the SMP. Typically, these forces may be applied to the SMP by zone drawing, or hydrostatic extrusion, or die drawing, or rolling, or roll drawing, or compression moulding. Alternatively any combination of these forces may be applied to the SMP Preferably, the SMP is heated during or prior to application of the one or more of these forces to the SMP. The application of heat to the SMP prevents the SMP from rupturing which may otherwise occur on application of one or more of these forces. Preferably, the SMP is heated to, close to, or above its Tg.

Preferably, the step of processing the shape memory material includes the addition of particles to the SMP. The particles help to conduct and distribute the heat more quickly to the SMP thus reducing the heating period which would otherwise be required in a less conductive material. The particles also help distribute the heat more evenly over the SMP providing an orientated SMP which has more consistent properties throughout. Preferably, the particles include mineral particles, ceramic particles, or combinations thereof. Preferably the particles are biodegradable inorganic particles. The particles may also be magnetic or photo sensitive particles.

After processing the SMP in this way, the SMP is now orientated and thus contains trapped energy which is later released during the relaxing step. The energy released during the relaxing step helps drive the shape change of the SMP. The trapped energy of the orientated SMP is released by stimulating molecular motion of the orientated SMP.

Preferably, stimulation of molecular motion is achieved by the application of energy to the SMP from an external source. Preferably, the energy applied is in the form of heat. Preferably, the SMP is heated above the glass transition temperature (Tg) of the SMP. Alternatively or additionally, the relaxing step and thus the release of trapped energy from the SMP may be prompted or triggered by the application of a different form of energy, for example, a magnetic field, an electric current, ultrasound, electromagnetic radiation such as microwaves, visible and infrared light, or by a combination of any one of these forms of energy.

Stimulating molecular motion of the SMP may also be achieved by exposing the orientated SMP to a plasticizer. Exposure of the SMP to a plasticizer reduces the Tg of the SMP, thus increasing its molecular mobility. In this way, the molecular mobility of the orientated SMP may be increased sufficiently to cause the orientated network to relax. Where exposure of the orientated SMP to a plasticizer is not sufficient to relax the SMP, energy, in the form of heat for example, may also be applied to the SMP. In this way, the orientated SMP can be relaxed at a temperature less than would be necessary where the SMP is relaxed using heat alone. As such, the SMP can be shaped at lower temperatures, thus allowing the addition of temperature sensitive materials to the SMP. Temperature sensitive materials may include, for example, releasable bioactive agents such as monobutyrin, bone marrow aspirate, angiogenic and osteogenic factors.

Plasticizers may be in the form of a volatile liquid or a gas. Examples of gaseous plasticizers include but are not limited to, oxygen, nitrogen, carbon dioxide, sulphur dioxide, ammonia, methane, ethane, butane, propane, hexane, decane, ethene, propene, butene, hexene, dodecanene, ethyne, and butyne. Examples of liquid plasticizers include but are not limited too, water, inorganic aqueous solutions such as sodium chloride solution, cyclic alkanes, such as cyclohexane and methylcyclohexane, cyclic alkenes, such as benzene and toluene, cyclic alkynes, halogen substitute alkanes, alkenes, and alkynes, such as carbon tetrachloride and chloropropane, oxygen substituted hydrocarbons, such as ethylene oxide and ethoxy hexane, aldehydes, such as hexanal, ketones, such as cyclohexanone, alcohols, such as methanol and ethanol, esters, such as buylpropionate, nitrogen substituted hydrocarbons, such as amine-triethylamine, and sulphur substituted hydrocabons, such as butane thiol and diethyl sulphide.

The energy stored in the SMP can either be completely released or partially released leading to a completely relaxed or partially relaxed SNAP. The resulting SMP is then known as a pre-relaxed SNAP. Once the SNAP is fully relaxed it can not be further relaxed unless reprocessed or re-orientated.

Ideally, the step of controlling the conditions under which the orientated SMP is at least partially relaxed includes placing at least part of the orientated SMP in a mould. The shape of the mould determines the third or final shape of the SMP and prevents the SNAP from returning to its original or first shape.

The mould may be of similar dimensions to the second shape and thus restrict the polymer to a third shape very similar to the second shape. Alternatively the mould may be of different dimensions, thus allowing the polymer to relax to a third shape substantially different to the first and second shapes. Complex moulds can be used to form pre-relaxed SMPs with complex shapes.

Where a plasticizer is used to relax the orientated SMP instead of or in addition to the application of energy, the mould may be porous or perforated, for example, to allow the direct contact of the orientated SMP with the plasticizer.

The step of controlling the conditions under which the orientated shape memory material is at least partially relaxed may also include control of the energy added to the SMP when relaxing the orientated SMP. Where heat is used as the energy source, variations in the temperature and period of exposure will result in shaped SMP having different properties. For example, where the SMP is exposed to heat for a short period of time, the SMP, although it will have formed ifs final shape within the mould, will have only given up part of its trapped energy and thus only have partially relaxed. Such a shaped SMP will be capable of further relaxing. This is particularly advantageous where it may be necessary to alter the dimensions, but not necessarily the overall shape, of the final shaped SMP. For example, where the final SMP is in the shape of a fastening bolt having a screw thread. In this case, the dimensions of the final fastening bolt shape can be altered somewhat to cater for dimension tolerances in a nut having a threaded receiving bore thus providing a bolt which can be more securely fitted in such a threaded bore.

Varying the orientation and relaxation of different sections of the SMP will also help tailor the final shape of the SMP.

When a final shape is required having unalterable dimensions, the SMP, whilst in the mould, can be exposed to heat for a longer period of time ensuring that the orientated SMP has released all its trapped energy and is thus fully relaxed. The addition of further energy or the further subsequent heating of such a relaxed SMP will not alter its dimensions. This is particularly useful when a device of exact and fixed shape and dimensions is required regardless of whether it may be subjected to external energy sources, such as heat, when used.

The particles added to the polymer during the processing step also help control the conditions under which the orientated SMP is at least partially relaxed. The particles help conduct the heat or other applied energy more evenly through the SMP, ensuring that the relaxing is consistent throughout the SMP, thus producing a pre-relaxed SMP having consistent properties throughout. The particles also help reduce the processing and controlling times by conducting the heat or other applied energy more quickly through the SMP than would otherwise occur. The addition of particles also helps improve subsequent machining of the shaped SMP where desired.

Generally, the larger the size of the particles added to the SMP, the longer it will take the orientated SMP to relax. This longer relaxation time could advantageously be used to tailor the shape of the relaxing SMP as the processing time is increased.

Suitable particles include but are not limited to inorganic particles such as buffers, radiopaque agents, osteoconductive agents, calcium, sodium, potassium, magnesium, barium, zirconium, bismuth, silver, gold, copper, zinc or any combination thereof. Preferably, the particles are crystalline calcium, sodium, zirconium, bismuth, barium, silicon, tungsten or magnesium salt.

Optionally, the particles can be calcium carbonate, calcium hydrogen carbonate, calcium phosphate, dicalcium phosphate, tricalcium phosphate, magnesium carbonate, sodium carbonate, hydroxyapatite, bone, phosphate glass, silicate glass, magnesium phosphate, sodium phosphate, barium sulphate, barium carbonate, zirconium sulphate, zirconium carbonate, zirconium dioxide, bismuth trioxide, bismuth oxychloride, bismuth carbonate, tungsten oxide or any combination thereof.

The particles can have a range of sizes and geometries. For example, the particles may be the shape of a needle, cube, platelet, fibre or sphere. Preferably the particles are shaped to enhance the mechanical properties of the SMP. The particle size is typically between 10 nm and 1 mm.

Typically, inorganic particles that act as buffers improve strength retention of degradable systems by reacting with the acidic breakdown products of the amorphous SMP.

Typical radiopaque agents include barium sulphate, barium carbonate, zirconium sulphate, zirconium carbonate, zirconium dioxide, bismuth trioxide, bismuth oxychloride, bismuth subcarbonate and tungsten oxide.

Typical osteogenic agents include calcium carbonate, calcium phosphate, dicalcium phosphate, tricalcium phosphate, hydroxyapatite, bone, phosphate glasses, silicate glasses, magnesium phosphate and sodium phosphate.

The particles may be pre-treated with a coupling agent such as a fatty acid, fatty acid anhydride or siloxane in order to enhance the properties of the SMP.

The method, useful for producing shape memory materials with complex geometries, is also useful for producing structural assemblies of shape memory polymers with other solid elements such as metals, polymers and ceramics.

According to another aspect of the present invention, there is provided a system for manufacturing a pre-relaxed shape memory polymer comprising a shape memory polymer as hereinbefore described and a mould.

Preferably, the mould is a complex mould for forming complex shapes of the shape memory polymer.

Preferably, the cavity of the mould has a modified surface to determine when the shape memory polymer has at least partially relaxed to form the third configuration. For example, the modified surface of the cavity can be pressure sensitive. In this way, as soon as the SMP has relaxed to form the third configuration or shape, the shaped SMP can be removed from the mould. This ensures that the SMP is relaxed for the minimum period of time resulting in a partially relaxed SMP which can be further relaxed at a later stage if required.

Generally, the SMP can be modified to produce particular desirable characteristics. The desired characteristics will depend largely on the end use of the pre-relaxed shape memory polymer.

Therefore, according to yet a further aspect of the present invention, there is provided a device including the pre-relaxed SMP as hereinbefore described.

The SMP can be of a resorbable, amorphous polymer composition or a non-resorbable, amorphous polymer composition. The SMP can be a homo polymer or a co-polymer, both of which can be linear, branched or cross-linked. The copolymer may comprise a component selected from a group consisting of glycolide, lactide, ethylene glycol or ε-caprolactone. For example, the copolymer can include a polylactide-co-glycolide, such as Poly(D,L-lactide-co-glycolide), or poly(methyl methacrylate), or poly(ethyl methacrylate) or other amorphous acrylic based polymers and copolymers. The copolymer can include an amorphous polymer composition and at least one mobile polymer and/or one rigid polymer.

Alternatively, the copolymer may include a semi-crystalline polymer and at least one mobile polymer and/or one rigid polymer. The mobility of a polymer refers to its ability to soften on application of heat. An SMP may have different areas of mobility relating to the different polymer compositions at different locations along the SMP composite. This allows different parts of the SMP to be orientated and relaxed at different temperatures and rates, thus allowing a finer control or tailoring of the final shape to be exercised. A rigid polymer is a polymer which demonstrates less mobility than a mobile polymer. The mobile polymer can include polyethylene glycol, or ϵ-caprolactone, or glycolide, or D,L lactide and the rigid polymer can include D-lactide or L-lactide. The co-polymer can be a random arrangement of monomers or a repetitive and sequenced arrangement of monomers.

Examples of synthetic degradable SMP material include but are not limited to polyhydroxy acids, including polylactide (PLA) based homo and co-polymers such as poly(L-lactic acid) (PLLA), poly(D-lactic acid) (PDLA), poly(D,L-lactic acid) (PDLLA), PLLA-co-PDLLA, PLLA-co-PGA (where PGA is polyglycolide), PDLA-co-PGA, PDLLA-co-PGA, PLLA-co-PCL (where PCL is ϵ-polycaprolactone), PDLLA-co-PCL, PDLA-co-PCL. Co-polymers with poly (ethyleneglycol) (PEG) such as PLLA-co-PEG, PDLA-co-PEG, PDLLA-co-PEG are also suitable examples of synthetic degradable SMP material. Further examples include co-polymers containing three or more of the following blocks: PLA, PEG, PCL or PGA. Polyanhydrides, poly (hydroxybutyric acid), poly(hydroxyvaleric acid), poly(pseudo aminoacids), poly(hydroxyalkanoate) and blends and co-polymers thereof.

Examples of natural biodegradable SMP material include but are not limited to polysaccharides such as alginate, dextran, cellulose, collagen, and chemical derivatives thereof. Further examples include substitutions and additions of chemical groups such as, for example, alkyl, alkylene, hydroxylations, oxidations, and other modifications routinely made by those skilled in the art. Proteins such as abumin, zein and co-polymers and blends thereof, alone or in combination with synthetic polymers are also suitable examples of natural biodegradable SMP material.

Examples of synthetic SMP material include but are not limited to polyphosphazenes, poly(vinyl alcohols), polyamides, polyester amides, poly(amino acids), polyanhydrides, polycarbonates, polyalkylenes, polyacrylamides, polyalkylene glycols, polyalkylene oxides, polyalkylene terephtalates, polyortho esters, polyvinyl ethers, poly vinyl esters, poly vinil halides, polyvinylpyrrolidone, polyesters, polysiloxanes, polyurethanes, polyacrylates such as poly (methyl methacrylate), poly(ethyl methacrylate), poly(butyl methacrylate), poly(isobutyl methacrylate), poly(phenyl methacrylate), poly(methyl acrylate), poly(isopropyl acrylate), poly(isobutyl acrylate) and poly(octadecyl acrylate), and co-polymers thereof. Further examples include poly (ethylene terephthalate), poly(ethylene), polystyrene, polycarbonate, polysulfones, polyethersulfone, polyetherimide and polypropylene.

Examples of synthetically modified natural SMP material include but are not limited to cellulose derivatives such as alkyl celluloses, hydroxyalkyl cellulose, cellulose ethers, cellulose esters, nitrocelluloses and chitosan. Examples of cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate and cellulose sulphate sodium salt.

The SMP can include a releasable bioactive agent. These agents are included to help promote bone regrowth. Examples include bone morphogenic proteins, antibiotics, anti-inflammatories, angiogenic factors, osteogenic factors, monobutyrin, thrombin, modified proteins, platelet rich plasma/solution, platelet poor plasma/solution, bone marrow aspirate, and any cells sourced from flora or fauna, such as living cells, preserved cells, dormant cells, and dead cells. Other bioactive agents known to one of ordinary skill in the art may also be used. Alternatively or additionally, the SMP can include a porogen, such as sodium chloride. This is particularly useful where the SMP device is required to promote cell growth.

Further areas of applicability of the present invention will become apparent from the detailed description provided hereinafter. It should be understood that the detailed description and specific examples, while indicating preferred embodiments of the invention, are intended for purposes of illustration only and are not intended to limit the scope of the invention.

BRIEF DESCRIPTION OF THE DRAWINGS

The accompanying drawings, which are incorporated in and form a part of the specification, illustrate embodiments of the present invention and together with the written description serve to explain the principles, characteristics, and features of the invention. In the drawings.

DETAILED DESCRIPTION OF THE EMBODIMENTS

Figure 1A:
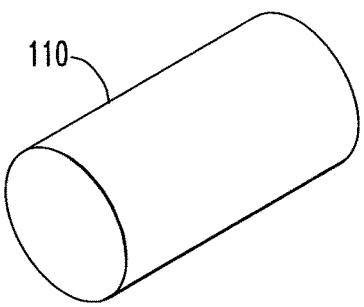
FIGS. 1A to 1D show a schematic illustration of a method, according to the present invention, for manufacturing a pre-relaxed shape memory polymer device in the form of a threaded screw.
Figure 1B:
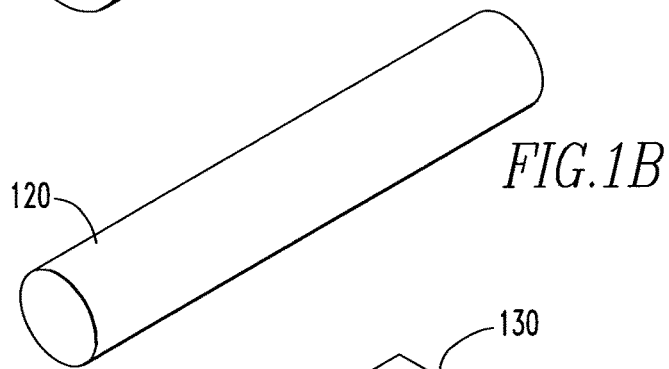
Figure 1C:
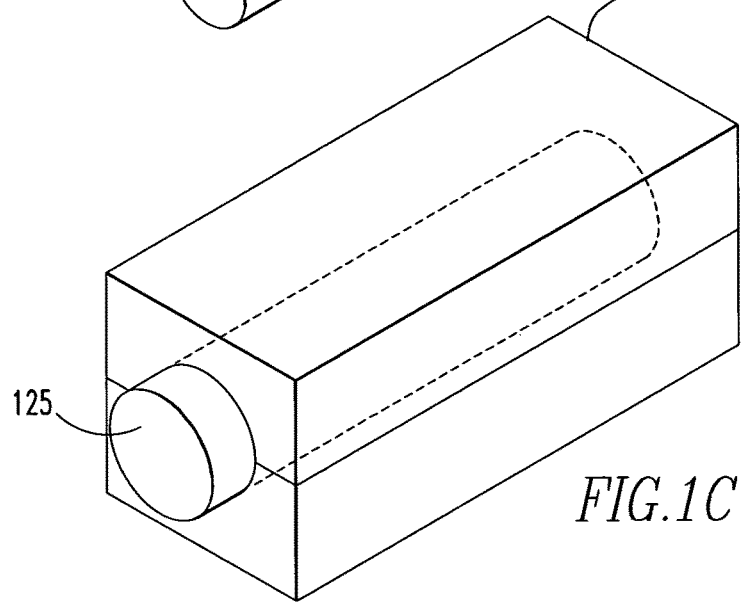
Figure 1D:
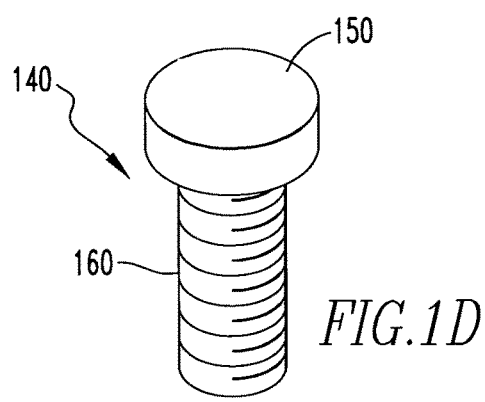
Figure 2A:
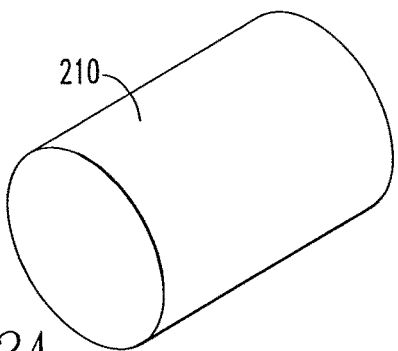
FIGS. 2A to 2E show a schematic illustration of a method, according to the present invention, for manufacturing a pre-relaxed shape memory polymer device in the form of a cylindrical rod.
Figure 2B:
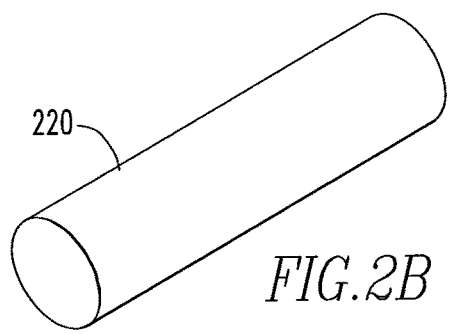
Figure 2C:
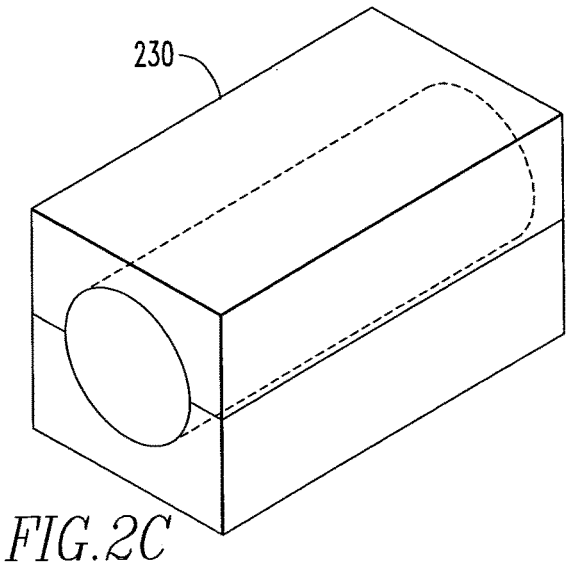
Figure 2D:
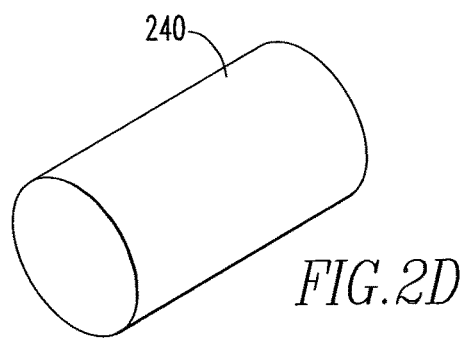
Figure 2E:
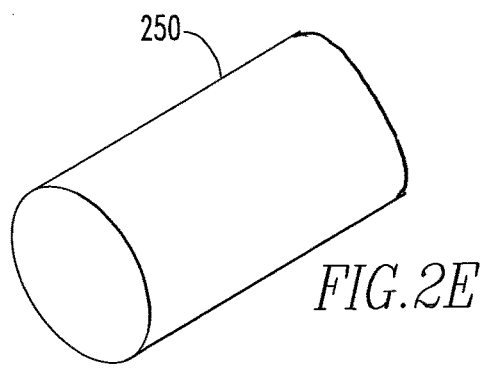

The following description of preferred embodiments is merely exemplary in nature and is in no way intended to limit the invention, its application, or uses.

Preparation of Orientated Shape Memory Polymer

The following description is given by way of example only of an embodiment of processing a SMP according to the present invention to form an orientated SMP and with reference to the examples describing embodiments of how the orientated SMP can be relaxed in a controlled manner to form a pre-relaxed SMP according to the invention.

In this embodiment the SMP, amorphous poly(D,L lactide-co-glycolide), was mixed with 35% w/w $CaCO_3$ particles (PLC). The mixture was prepared in a twin screw extruder to form fibres of the mixture. The fibres were palletised and consolidated to form isotropic cylindrical rods 110, 210, 410, and 510 with various diameters ranging from 5 mm to 20 mm using a ram extrusion technique. Isotropic rods thus formed having diameters of 5 mm, 18 mm and 20 mm were orientated by die drawing using a conical die at 60° C. and a drawing speed of 20 mm/min to form orientated rods 120, 220, 420 and 520 having diameters of 3 mm, 8 mm and 9 mm, respectively.

Example 1

A prepared orientated SMP as described above in the form of a cylindrical rod 120 having a diameter of 8 mm was placed into a mould 130 having a threaded screw shaped cavity such that an end part 125 of the orientated rod 120 protrudes from an end of the mould 130. The mould 130 and orientated rod 120 are immersed in a water bath at 80° C. for 60 seconds and then into a water bath at 20° C. for another 60 seconds to allow the oriented SMP to relax, resulting in a pre-relaxed screw 140 that has a head portion 150, which expanded freely without the mechanical restraint of the mould 130, having a radius similar to the isotropic rod 110, and a threaded portion 160 having dimensions determined by the dimensions of the mould 130. On removal of the screw 140 from the mould, the addition of further energy to the threaded portion will cause the threaded portion 160 of the screw 140 to further relax and expand radially whilst the head portion 150 will remain substantially of the same radius. Both threaded portion 160 and head portion 150 will remain substantially the same shape. This expansion moulding technique can be applied to other mould geometries.

Example 2

A sample of prepared orientated SMP as described above in the form of a cylindrical rod 220 having a diameter of 3 mm was placed into a mould 230 having a cylindrical cavity that has substantially the same cavity radius as the radius of the orientated rod 220. The orientated rod 220 was partially relaxed by heating the mould 230 and orientated rod 220 in a fan assisted oven at 80° C. for 5 minutes to produce a pre-relaxed cylindrical rod 240 that has substantially the same radius as the orientated cylindrical rod 220. The pre-relaxed cylindrical rod 240 is subsequently immersed in water at 80° C. to allow further relaxation without mechanical constraints. The partially relaxed rod 240 was immersed in the water until the diameter of the rod 240 did not appreciably change resulting in a twice-relaxed cylindrical rod 250 having a radius greater than the orientated cylindrical rod 220 but less than isotropic cylindrical rod 210.

This process was repeated with further sample rods 220 with partial relaxing times from 0 to 120 minutes. It was found that the degree of recovery of the original diameter of the isotropic cylindrical rod 210 decreased with increased partial relaxing time as can be seen from table 1. It was concluded that by partially relaxing the oriented rods 220 into a suitable mould the degree of recovery of the initial shape, in this case length and diameter, of the isotropic cylindrical rod 210 can be varied from substantially 0% for long partial relaxing times where the orientated rod 220 is substantially fully relaxed to almost 100% for short partial relaxing times where the orientated rod 220 is practically not relaxed at all but still contains substantially all the energy imparted thereto by orientation.

TABLE 1

Table 1: Effect of partial relaxation time at 80° C. on the degree of recovery of die drawn PLC rods.

| Pre-relaxation time (min) | Diameter of relaxed rod (mm) | Diameter of fully pre-relaxed rod (mm) | Degree of recovery (%) |
| --- | --- | --- | --- |
| 0 | 3.05 | 5.20 | 100 |
| 5 | 3.05 | 5.20 | 100 |
| 15 | 3.05 | 5.20 | 100 |
| 20 | 3.05 | 4.35 | 60 |
| 30 | 3.05 | 3.65 | 28 |
| 60 | 3.05 | 3.17 | 5 |
| 120 | 3.05 | 3.09 | 2 |

Example 3

Figure 3:
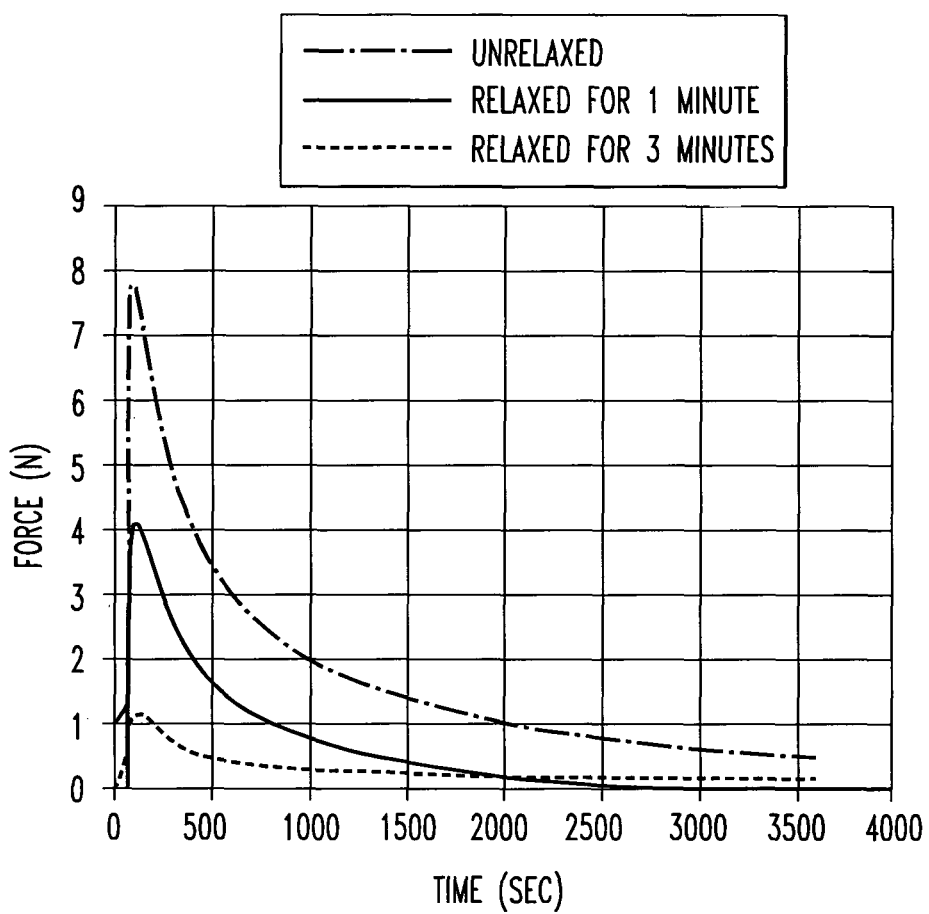
FIG. 3 is a graph showing the effect of different relaxing times on the expansion force along the radial direction of die-drawn shape memory polymer cylindrical shaped rods.

FIG. 3 shows a graph plotting the expansion force in Newtons (N) against time for samples of prepared orientated SMP as described above in the form of cylindrical rods having a diameter of 3 mm. Some of the samples were partially relaxed in a two piece long metal mould having a cylindrical cavity 3 mm in diameter at 80° C. with a fan assisted oven for different periods of time and other samples were not relaxed at all. On further relaxing these cylindrical samples at 60° C., the expansion force along the radial direction of the cylindrical samples was measured for specimens having the same volume and partially relaxed for 0, 1 and 3 minutes. The graph shows that the orientated sample rods which had not been partially relaxed have a greater expansion force than the partially relaxed orientated sample rods. The expansion force of the sample rod was observed to decrease with an increase in time spent partially relaxing the sample rod. For example, 1 minute spent partially relaxing a sample rod in the mould significantly reduced the expansion force of the sample rod when further relaxed, whilst 3 minutes spent partially relaxing a sample rod in the mould reduced the expansion force yet further. It was concluded that the maximum expansion force rapidly decreases due to molecular re-arrangement of the oriented network.

Example 4

Figure 4A:
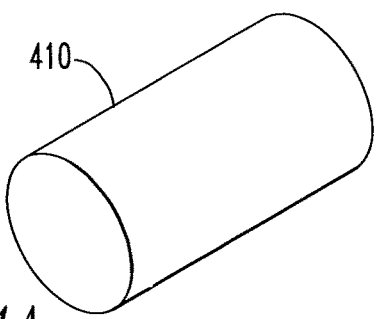
FIGS. 4A to 4D show a schematic illustration of a method, according to the present invention, for manufacturing a pre-relaxed shape memory polymer device of square cross section.
Figure 4B:
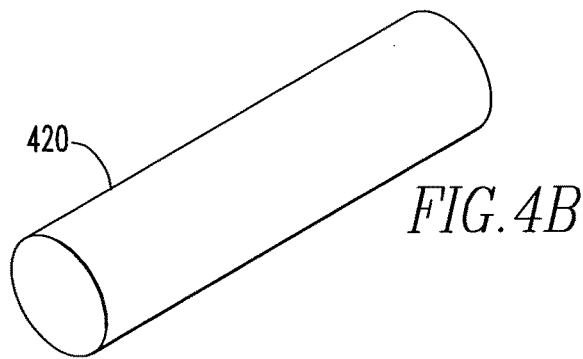
Figure 4C:
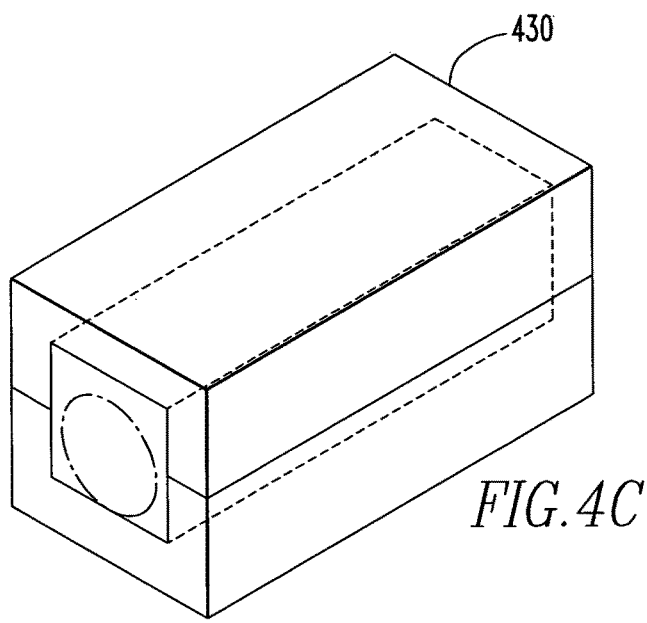
Figure 4D:
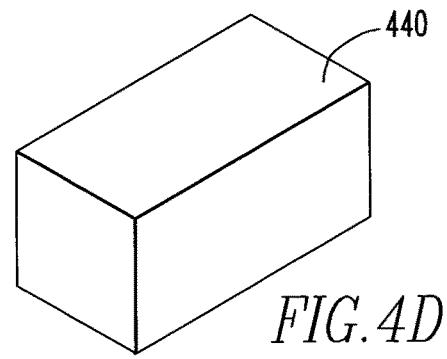

A prepared orientated SMP as described above in the form of a cylindrical rod 420 having a diameter of 9 mm is placed in a cavity mould 430. The cavity of the mould 430 has a 14 mm by 14 mm square cross-section. The mould 430 and orientated rod 420 are immersed in hot water at 80° C. for 2 minutes to allow the orientated rod 420 to relax to produce a pre-relaxed bar 440 shorter in length than the cylindrical rod 420 and with a square cross section having substantially the same dimensions as the square cross-section of the cavity of the mould 430. The pre-relaxed bar 440 is clearly illustrated in FIG. 4D.

Example 5

Figure 5A:
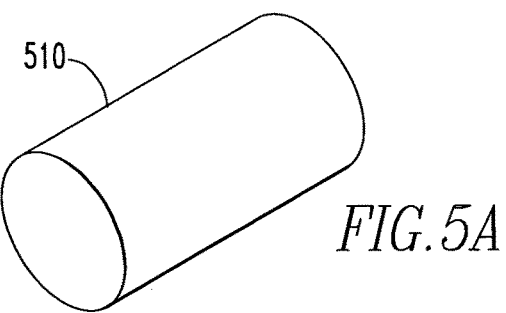
FIGS. 5A to 5D show a schematic illustration of a method, according to the present invention, for manufacturing a pre-relaxed shape memory polymer device of triangular cross section.
Figure 5B:
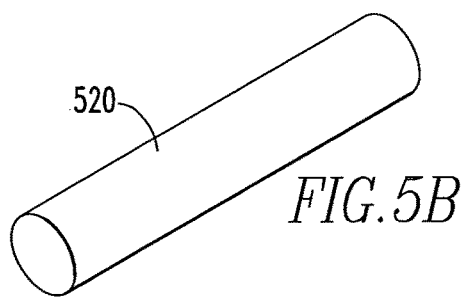
Figure 5C:
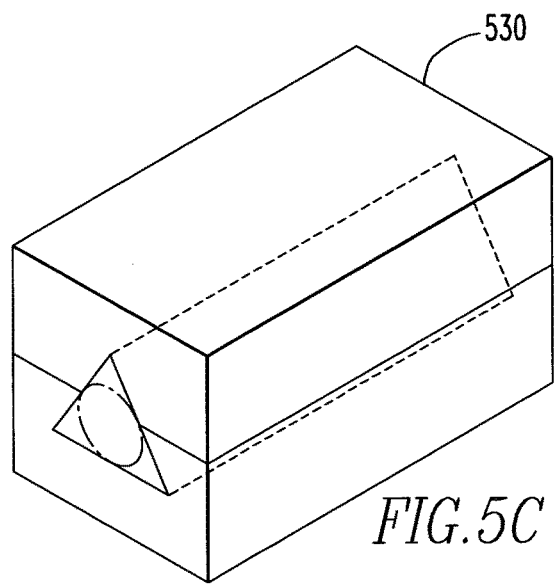
Figure 5D:
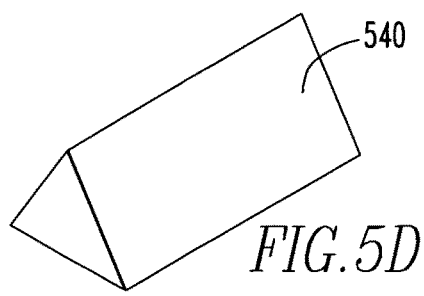

A prepared orientated SMP as described above in the form of a cylindrical rod 520 having a diameter of 9 mm is placed in a cavity mould 530. The cavity of the mould 530 has a 16 mm equilateral triangle cross-section. The mould 530 and orientated rod 520 are immersed in hot water at 80° C. for 2 minutes to allow the orientated rod 520 to relax to produce a pre-relaxed SMP 540 shorter in length than the cylindrical rod 520 and having a triangular cross section with substantially the same dimensions as the triangular cross-section of the cavity of the mould 530. The pre-relaxed SMP 540 is clearly illustrated in FIG. 5D.

Where plasticisers are used instead of or in addition to energy, the plasticiser must come into direct contact with the SMP. This can be achieved, for example, by employing a porous or perforated type mould. On introduction of the porous mould containing the orientated SMP into an environment containing a plasticiser, the plasticiser will pass through the mould via the pores and directly contact the orientated SMP to stimulate molecular motion and thus relaxation of the orientated SMP. It will be appreciated that energy in the form of heat for example, may also be used in conjunction with the plasticiser to promote relaxation of the orientated SMP. For example, the plasticiser itself may be used to transfer energy to the SMP by heating the plasticiser.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

The invention claimed is:

1. A pre-relaxed three-dimensional shape memory polymer material having a molded configuration made by the method comprising:
    consolidating a material including an amorphous shape memory polymer material to form an isotropic cylinder in a first configuration;
    orientating the amorphous shape memory polymer material in the isotropic cylinder having the first configuration thereby forming an orientated shape memory polymer material having a second configuration;
    forming a mold about the orientated shape memory polymer material having the second configuration, such that the mold constrains the first portion of the oriented shape memory polymer material and the mold does not constrain a second portion of the oriented shape memory polymer material;
    applying a source of energy to, and/or exposing to at least one plastizer the orientated shape memory polymer material having the second configuration while the first portion is within the mold, thereby at least partially relaxing the orientated shape memory polymer material into a third configuration in which only the first portion conforms to the configuration of the mold and in which the first portion retains more shape memory potential than the second portion;
    ceasing the application of the source of energy to the shape memory polymer material when the shape memory polymer material is formed into the third configuration; and removing the mold when the shape memory polymer material is formed into the third configuration and the application of the source of energy, and/or exposure to at least one plastizer has ceased, wherein the shape memory polymer material having the third configuration retains its configuration unless a source of energy is applied to, and/or at least one plastizer is exposed to the shape memory polymer material in the third configuration, the retention of the shape memory polymer material in the third configuration after ceasing the application of the source of energy to, and/or the exposure to at least one plasticer, and the removal of the mold being greater than the retention of a configuration formed of the same shape memory polymer material treated by the same method except for not being in a mold when at least partially relaxed, and wherein the first, second, and third configurations are different to each other, and molecular motion of the third pre-relaxed configuration is stimulated to trigger further relaxation, wherein the shape memory polymer comprises an amorphous polymer.

2. The material of claim 1, wherein the source of energy is selected from the group consisting of a magnetic field, an electric current, ultrasound, electromagnetic radiation, heat by convection, heat by conduction, radiation or any combination thereof.

3. The shape memory polymer material of claim 1, wherein the shape memory polymer is a copolymer.

4. The shape memory polymer material of claim 3, wherein the copolymer comprises a component selected from a group consisting of glycolide, lactide, ethylene glycol, or $\epsilon$-caprolactone.

5. The shape memory polymer material of claim 3, wherein the copolymer includes the amorphous polymer and at least one mobile and/or rigid polymer.

6. The shape memory polymer material of claim 3, wherein the copolymer includes a semi-crystalline polymer and at least one mobile polymer and/or one rigid polymer.

7. The shape memory polymer material of claim 5, wherein the mobile polymer includes polyethylene glycol, or $\epsilon$-caprolactone, or glycolide, or D,L lactide and the rigid polymer includes D-lactide or L-lactide.

8. The shape memory polymer material of claim 1, wherein the shape memory polymer includes particles such as mineral particles, or ceramic particles, or magnetic particles, or photosensitive particles, or any combination thereof.

9. The shape memory polymer material of claim 1, wherein the shape memory polymer includes one or more releasable bioactive agents.

10. The shape memory polymer material as claimed in claim 9, wherein the one or more releasable bioactive agents include bone morphogenic proteins, antibiotics, anti-inflammatories, angiogenic factors, osteogenic factors, monobutyrin, thrombin, modified proteins, platelet rich plasma/solution, platelet poor plasma/solution, bone marrow aspirate, cells sourced from plants or animals.

11. The shape memory polymer material of claim 1, wherein the shape memory polymer includes a cell growth promoter.

12. The shape memory polymer material of claim 1, the method further comprising applying a source of energy to, and/or exposing to at least one plastizer the third configuration after removal of the mold thereby fully relaxing the third configuration into a fourth configuration that is substantially the same configuration as the first, configuration.

13. The shape memory polymer material of claim 12, wherein the source of energy is selected from the group consisting of a magnetic field, an electric current, ultrasound, electromagnetic radiation, heat by convection, heat by conduction, radiation or any combination thereof.

14. The shape memory polymer material of claim 1, wherein the orientating of the unorientated shape memory polymer material having a first configuration thereby forming an orientated shape memory polymer material having a second configuration comprises orientating by zone drawing, hydrostatic extrusion, die drawing, rolling, roll drawing, compression moulding, or any combination thereof.

* * * * *